US012677805B2

(12) United States Patent
Yang et al.

(10) Patent No.: US 12,677,805 B2
(45) Date of Patent: Jul. 14, 2026

(54) IMAGE ACQUISITION SYSTEM FOR HEALTH EVALUATION OF LACTATING COW TEAT

(71) Applicant: QINGDAO AGRICULTURAL UNIVERSITY, Qingdao City (CN)

(72) Inventors: Yongxin Yang, Qingdao City (CN); Tao Wu, Qingdao City (CN); Rongwei Han, Qingdao City (CN); Rongbo Fan, Qingdao City (CN); Qijing Du, Qingdao City (CN); Qinggang Luan, Qingdao City (CN); Xiaowei Zhao, Qingdao City (CN); Hongning Jiang, Qingdao City (CN); Zhongna Yu, Qingdao City (CN); Jun Wang, Qingdao City (CN)

( * ) Notice: Subject to any disclaimer, the term of this patent is extended or adjusted under 35 U.S.C. 154(b) by 173 days.

(21) Appl. No.: 18/626,355

(22) Filed: Apr. 4, 2024

(65) Prior Publication Data

US 2024/0357990 A1    Oct. 31, 2024

(30) Foreign Application Priority Data

Apr. 26, 2023    (CN) .......................... 202310462760.3

(51) Int. Cl.
   *A01K 29/00*      (2006.01)
   *A61B 5/00*      (2006.01)
   *G03B 17/56*      (2021.01)

(52) U.S. Cl.
   CPC .......... *A01K 29/005* (2013.01); *A61B 5/4312* (2013.01); *G03B 17/561* (2013.01)

(58) Field of Classification Search
CPC .. A01K 29/005; A61B 5/4312; A61B 5/0077; A61B 3/40; A61B 2503/40; G03B 17/561; G03B 17/563; F16M 13/00; F16M 13/005; F16M 13/02
See application file for complete search history.

(56) References Cited

U.S. PATENT DOCUMENTS

| | | | | |
|---|---|---|---|---|
| 2016/0091779 A1* | 3/2016 | Jodoin | ................. | G03B 17/563 |
| | | | | 396/428 |
| 2019/0080160 A1* | 3/2019 | Wee | ......................... | G06F 18/22 |
| 2022/0167594 A1* | 6/2022 | Liao | .......................... | G06T 7/30 |
| 2022/0217950 A1* | 7/2022 | Song | .................... | A61B 5/7257 |

FOREIGN PATENT DOCUMENTS

| | | | | | |
|---|---|---|---|---|---|
| IT | 201800003013 A1 * | 8/2019 | ........... | G03B 17/563 |
| NL | 8602699 A * | 5/1988 | ............. | G01S 15/88 |

* cited by examiner

*Primary Examiner* — Christopher E Mahoney

(57) ABSTRACT

The current invention pertains to digital livestock breeding, focusing on a novel image acquisition system designed for assessing the health of lactating cow teats. Addressing challenges related to image capture quality and operational complexity in dairy cow teat examination, the solution comprises a guard plate, a telescopic column with a hinge mechanism, and a photo unit. Straps are positioned at each end of the guard plate, and an installation seat is located at the rotational juncture. The telescopic column includes a fixed cylinder pivotally attached to the guard plate and a movable column within it, extending beyond the fixed cylinder. Additionally, a fixed grip is mounted on one side of the fixed cylinder's outer wall. This innovation streamlines user-friendly shooting and adjustment processes while enabling timely cleaning of the lens and light-emitting device, ensuring image clarity.

9 Claims, 5 Drawing Sheets

IMAGE ACQUISITION SYSTEM FOR HEALTH EVALUATION OF LACTATING COW TEAT

TECHNICAL FIELD

The present invention relates to the field of digital breeding of livestock, in particular to an image acquisition system for health evaluation of lactating cow teats.

BACKGROUND ART

The health condition of the teat end of lactating dairy cows significantly impacts the prevalence of mastitis. A proficiently functioning sphincter encircling the teat canal in healthy cows exhibits timely contraction and relaxation, promptly constricting and sealing the teat canal post-milking. The contracted sphincter, coupled with reconstituted keratin, effectively closes off the teat canal, thereby establishing a physical barrier to prevent bacterial invasion. The main factors affecting the health of the teat end are the vacuum intensity of milking apparatus and pulsation settings, the integrity of the milking liner, and post-milking teat disinfection. Elevated vacuum levels can induce teat tissue damage through excessive suction during milking, while insufficient vacuum intensity prolongs milking duration, thereby increasing exposure time to potential teat injury. The results of related studies indicate a negative correlation between dairy cow teat end health and somatic cell counts. Moreover, in production, the score of the teat end of cows is also used to evaluate the health level of the teat of lactating cows. However, the current method for capturing images of lactating cow teats primarily relies on mobile phones or cameras. This procedure entails the deployment of devices such as mobile phones or cameras beneath the bovine abdomen. Nevertheless, the insufficient illumination and positioning of devices within the environment present obstacles in obtaining images that conform to the prescribed standards. Therefore, this proposal advocates for the implementation of an image acquisition system designed for assessing the health of lactating cow teats.

SUMMARY

The present invention introduces an image acquisition system designed for health evaluation of lactating cow teats. It aims to resolve challenges posed by inconvenient shooting protocols and operational intricacies inherent in conventional cow teat image acquisition devices.

To achieve the above purpose, the present invention adopts the following technical scheme:

An image acquisition system designed for health evaluation of lactating cow teats, including a guard plate, a telescopic column hinged on the guard plate, and a photographic unit affixed to the telescopic column. Both ends of the guard plate are installed with straps, an installation seat is arranged at the rotating connection on the guard plate. The telescopic column includes a fixed cylinder hinged to the guard plate and a movable column housed within the fixed cylinder. One end of the movable column protrudes beyond the exterior of the fixed cylinder. A stationary grip is installed on one side of the outer surface of the fixed cylinder, while a movable grip is installed on one side of the outer surface of the movable column;

The photographic unit includes a base pivotally attached to one end of the movable column, a camera apparatus mounted on the base, and supplementary lights. Additionally, the movable column is equipped with an adjustable unit to facilitate the rotation of the base, and the base is equipped with a cleaning unit;

The cleaning unit includes a hollow shaft connected to the base via rotational connection, a fixed pipe affixed to the periphery of the shaft, and a cleaning brush installed on the bottom surface of the fixed pipe, the bottom surface of the fixed pipe. Outlet canals are present on the bottom surface of the fixed pipe, which is interconnected with the shaft;

A purging mechanism is also installed in the movable column, intended for introducing air into the fixed cylinder and driving the shaft to rotate when the movable column contracts into the fixed pipe;

A detachable display mounting frame is affixed to the outer surface of the fixed cylinder. The display screen mounting frame is equipped with a display screen, which is connected to both connected with the shooting device and supplementary lights.

Through the aforementioned technical scheme, users can conveniently capture and adjust images, while also being able to promptly clean the lens of the shooting device and remove dust from the light-filling surface, thus ensuring the clarity of the acquired image.

As a further improvement of the aforementioned scheme, the base is a hollow structure wherein the shooting device and the supplementary lights are installed in the base. Mounting canals are arranged on the top surface of the base to accommodate the shooting device and supplementary lights, ensuring that the lens of the shooting device and lampshades of the supplementary lights are level with the top surface of the base.

Through the aforementioned technical scheme, it is convenient to clean the dust on the lens of the shooting device and the dust on the surface of the supplementary lights.

As a further improvement of the aforementioned scheme, the adjustable unit includes a storage barrel pivotally connected to a fixed grip, a transmission rod pivotally connected to the outer wall of the movable column, and a movable sleeve arranged outside the fixed grip. The movable sleeve is rotationally connected with the fixed grip, the outer of movable sleeve is encased with a driving bevel gear. Correspondingly, the outer surface of the storage barrel accommodates a driven bevel gear that meshes with the driving bevel gear. One end of the transmission rod extends into the storage barrel and can move axially within its confines. Additionally, two installation blocks are affixed to on the outer wall of the base, with one end of the movable column situated between them. Both sides of the outer wall of the movable column are secured with connecting shafts that rotate along with two installation blocks.

Through the aforementioned technical scheme, the pitch angle of the base can be easily adjusted to suit specific requirements, thereby ensuring optimal shooting angles for the shooting device.

As a further improvement of the aforementioned scheme, the transmission rod is located at one end of the storage barrel, where a limiting block is affixed to the periphery. The inner wall of the storage barrel features a longitudinal locating slot, into which one end of the limiting block extends, facilitating sliding movement along the slot. Furthermore, a friction ring is sleeved onto the outer surfaces of the two connecting shafts, with one end of the friction ring linked to the outer wall of the installation block.

Through the aforementioned technical scheme, a limitation arises wherein the transmission rod is restricted to movement solely along the radial direction of the storage barrel, without the ability to rotate relative to the storage barrel. Additionally, the inclusion of the friction ring introduces a resistance to the rotation of the base, serving to counterbalance the gravitational forces acting upon the base itself.

As an additional enhancement to the aforementioned scheme, a purging unit includes a fixed rod arranged in the movable column, a sealing block fixed on the inner side of the movable column and a pneumatic component arranged on the base for driving a rotating shaft. A sealed gas storage space is formed between the sealing block and the inner wall of the movable column near the base, with a spacer plate fixed within the gas storage space to divide it into gas chamber 1 and gas chamber 2. The active block is situated exterior to the gas storage space, with the side near the sealing block fixed with a piston rod 1 and a piston rod 2. The piston rod 1 extends to gas chamber 1 and is affixed with piston plate 1, while the piston rod 2 extends to gas chamber 2 and is affixed with piston plate 2. An elastic component is provided on the outer sleeve of piston rod 2 to facilitate the resetting of the active block. One end of the fixed rod is anchored to the inner wall of the fixed cylinder, cooperating with the active block. A connecting pipe is fixed to the base, with the shaft's bottom inserted into and connected to the connecting pipe. The periphery of the connecting pipe is fixedly connected with the gas pipe 2, where the other end of the gas pipeline 2 is connected with the gas chamber 2, while the gas chamber 1 is connected with the pneumatic component.

Through the aforementioned technical arrangement, the dust accumulated on the surface of the base can be effectively cleaned while restoring functionality.

As a further improvement of the above scheme, the pneumatic component includes a piston cylinder arranged on the top surface of the base, a piston plate 3 actively arranged in the piston cylinder, a transmission rack fixed on the three outer walls of the piston plate 3 and a transmission gear encased around the shaft. One end of the transmission rack extends to the outside of the piston cylinder and engages with the transmission gear. Additionally, one end of the piston cylinder is installed with a gas pipeline 1, and the other end of gas pipeline 1 is connected with the gas chamber 1.

Through the above technical scheme, the kinetic energy generated by air compression is utilized to drive the rotation of the shaft, enabling the cleaning brush to effectively clean the targeted area.

As a further improvement of the above scheme, a mounting sleeve is securely affixed to the top surface of the fixed cylinder, with locking bolts threaded onto the outer wall of the mounting sleeve. The lower section of the display screen mounting frame is firmly connected to an inserting rod, which is inserted into the mounting sleeve. One end of the locking bolts is linked to the outer wall of the inserting rod. Additionally, a data interface, interfacing with both the supplementary lights and the shooting device, is installed on the outer wall of the fixed cylinder. The display screen is subsequently connected to the data interface via a data line.

Through the above technical scheme, the disassembly and assembly of the display screen mounting frame are facilitated for greater convenience.

As a further improvement of the above scheme, a battery is installed in the base to provide power to both the shooting device and the supplementary lights. The battery is designed to be detachable for maintenance purposes. A maintenance port is positioned at the bottom of the base, which is sealed by a removable sealing cover.

Through the above technical scheme, it is convenient to replace the battery.

As a further improvement of the above scheme, a chute is implemented along the axial direction on one side of the outer wall of the fixed cylinder. This facilitates the extension of the other end of the movable grip through the chute to the exterior of the fixed cylinder.

Through the above technical scheme, on the one hand, it is convenient to manipulate the movable column, and on the other hand, it serves to prevent the movable column from dislodging out of the fixed cylinder.

Compared with the existing technology, the beneficial effects of the invention are that:

1. The waist canal device can be attached to the user's waist using the guard plate and strap. Subsequently, the position and angle of the shooting device can be conveniently adjusted using the telescopic column and adjustable unit, allowing the operator to capture images from the desired angle;
2. By incorporating the cleaning unit and purging unit, the movable column can be actuated to move while the fixed pipe is retracted, facilitating the wiping of dust or debris from the surface of the lens of the shooting device and the lampshade of the supplementary lights using the cleaning brush. Prior to dust wiping, the air discharged through gas chamber 2 can effectively purge dust from the top of the base, thus augmenting the overall cleaning efficacy.

Figure 1:
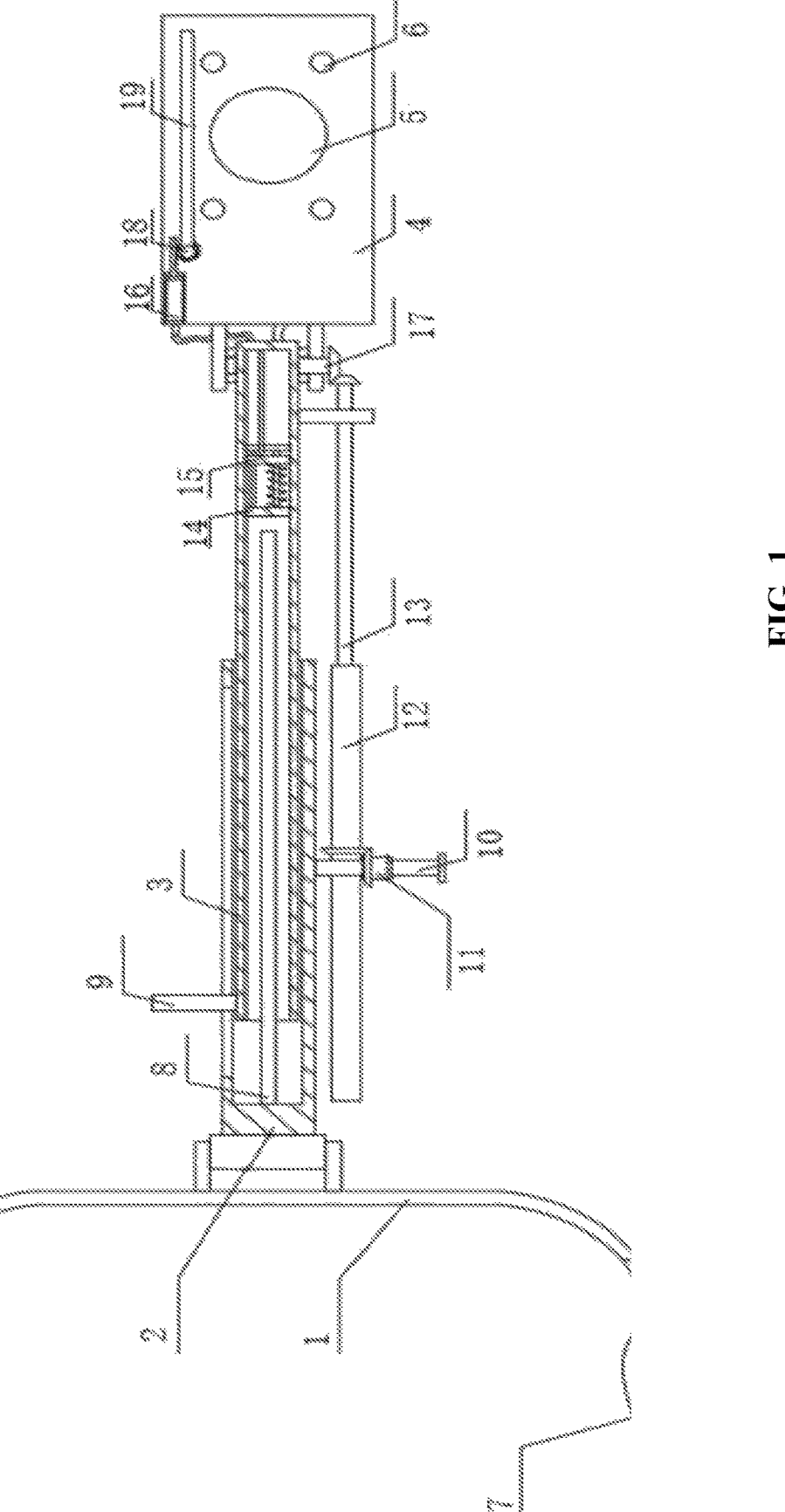
FIG. 1 is a top view profile of the present invention.

MAIN SYMBOL DESCRIPTION 1. guard plate; 2. fixed cylinder; 3. movable column; 4. base; 5. shooting device; 6. supplementary light; 7. strap; 8. fixed rod; 9. movable grip; 10. fixed grip; 11. movable sleeve; 12. storage barrel; 13. transmission rod; 14. active block; 15. sealing block; 16. piston cylinder; 17. connecting shaft; 18. shaft; 19. fixed pipe; 20. gas pipeline 1; 21. transmission gear; 22. cleaning brush; 23. piston rod 1; 24. piston rod 2; 25. spacer plate; 26. friction ring; 27. transmission rack; 28. connecting pipe; 29. sealing cover; 30. data interface; 31. display screen mounting frame; 32. inserting rod; 33. mounting sleeve; 34. gas pipeline 2.

DETAILED DESCRIPTION OF THE EMBODIMENTS

Combined with the attached diagram and the specific implementation method, the present invention is further elucidated. It is important to note that, in the absence of conflict, new embodiments can be derived from any combination of the described embodiments or technical features.

Example 1

Combined with FIGS. 1-5, an image acquisition system for health evaluation of lactating cow teats in this example, including a guard plate 1, a telescopic column hinged on the guard plate 1, and a photo unit mounted on the telescopic column, Both ends of the guard plate 1 are equipped with straps 7, with magic stickers installed on two straps 7. An installation seat is arranged at the rotating connection on the guard plate 1. The telescopic column includes a fixed cylinder 2 hinged on the installation seat and a movable column 3 set within the fixed cylinder 2. The outer wall of movable column 3 and the inner wall of fixed cylinder 2 have rough surfaces, facilitating a certain resistance to movement, thereby preventing easy displacement of the movable column 3. One end of the movable column 3 extends outside the fixed cylinder 2. A fixed grip 10 is mounted on the outer wall of one side of the fixed cylinder 2, while a movable grip 9 is installed on one side of the outer wall of the movable column 3. A chute is positioned along the axial direction on one side of the outer wall of the fixed cylinder 2, through which the other end of the movable grip 9 extends to the exterior of the fixed cylinder 2. The fixed grip 10 is designed to hold the fixed cylinder 2 securely, while the movable grip 9 facilitates the movement of the movable column 3.

The photo unit comprises a base 4, hinged at one end of the movable column 3, a shooting device 5 installed on the base 4, and supplementary lights 6. The base 4 is hollow in structure, accommodating both the shooting device 5 and the supplementary lights 6. Mounting canals are situated on the top surface of the base 4 for the installation of the shooting device 5 and supplementary lights 6. The lens of the shooting device 5 and lampshades of the supplementary lights 6 are flush with the top surface of the base 4.

The movable column 3 is equipped with an adjustable unit designed to drive the rotation of the base 4. This adjustable unit comprises a storage barrel 12, rotationally connected to the fixed grip 10, a transmission rod 13, rotationally connected to the outer wall of the movable column 3, and a movable sleeve 11 arranged outside the fixed grip 10. The movable sleeve 11 is rotationally connected to the fixed grip 10 and encloses a driving bevel gear on its outer surface. The storage barrel 12 is encased with a driven bevel gear that meshes with the driving bevel gear. Multiple anti-slip protrusions are fixed peripherally on the movable sleeve 11 to enhance grip. One end of the transmission rod 13 extends into the storage barrel 12 and can move along the axial direction of the storage barrel 12 and is capable of axial movement within it. Two installation blocks are fixed on the outer wall of the base 4, with one end of the movable column 3 situated between them. Both sides of the outer wall of the movable column 3 are fixed with a connecting shaft 17 that rotate with two installation blocks. The transmission rod 13, positioned at one end of the storage barrel 12, includes a limit block fixed to its periphery. A locating slot, aligned along the axial direction, is integrated into the inner wall of the storage barrel 12, allowing the limit block to slide within it. The engagement of the limit block within the locating slot ensures that the transmission rod 13 moves solely along the axial direction of the storage barrel 12. Additionally, vulcanized rubber friction rings 26 are fitted over the exterior of the two connecting shafts 17, with one end of each friction ring 26 attached to the outer wall of the corresponding installation block. These friction rings 26, relying on friction between them and the installation blocks, provide resistance during base 4 rotation, thereby counteracting the gravitational force of the base 4 itself and preventing unintended rotation in the absence of external force.

A detachable display screen mounting frame 31 is installed on the outer wall of the fixed cylinder 2. This mounting frame is equipped with a display screen, which is interconnected with both the shooting device 5 and the supplementary lights 6. The display screen can be easily disconnected from and reattached to the mounting frame 31 as needed. Additionally, the base 4 incorporates a storage battery intended for providing power to both the shooting device and the supplementary lights 6. This battery is designed to be removable for maintenance or replacement purposes. Furthermore, a maintenance port is situated at the base 4's underside, and its exterior is secured by a detachable sealing cover 29. The top surface of the fixed cylinder 2 is furnished with a mounting sleeve 33, onto which a locking mechanism comprising bolts is affixed along the outer wall of the mounting sleeve 33. The lower section of the display screen mounting frame 31 is rigidly attached to an inserting rod 32, which is inserted into the mounting sleeve 33. One end of the locking bolts is connected to the outer wall of the inserting rod 32 to ensure secure fixation. Moreover, a data interface (identified as 30) linked to the supplementary lights 6 and the shooting device 5 is integrated into the outer wall of the fixed cylinder 2. The display screen is connected to this data interface 30 via a data line for seamless communication and operational synergy.

The implementation principle of this example is as follows: Firstly, the guard plate 1 is secured to the user's waist using the straps 7. Then, the user holds the fixed grip 10 and manipulates the movable grip 9 to adjust the extension length of the movable column 3. Subsequently, the shooting device 5 is positioned beneath the teat of the cow. To alter the pitch angle of the base 4, the movable sleeve 11 is rotated, consequently rotating the storage barrel 12. This rotation of the storage barrel 12 drives the transmission rod 13 to rotate synchronously, thereby rotating the connecting shaft 17. When the movable sleeve 11 rotates in a particular direction, the base 4 tilts upward, whereas rotation in the opposite direction causes the base 4 to tilt downward. Following adjustment of the shooting angle, the shooting device 5 is controlled via the display screen to capture images, which are then transmitted in real-time to the display screen. Additionally, the display screen enables control of the supplementary lights 6, facilitating their activation or deactivation as necessary.

Example 2

Figure 2:
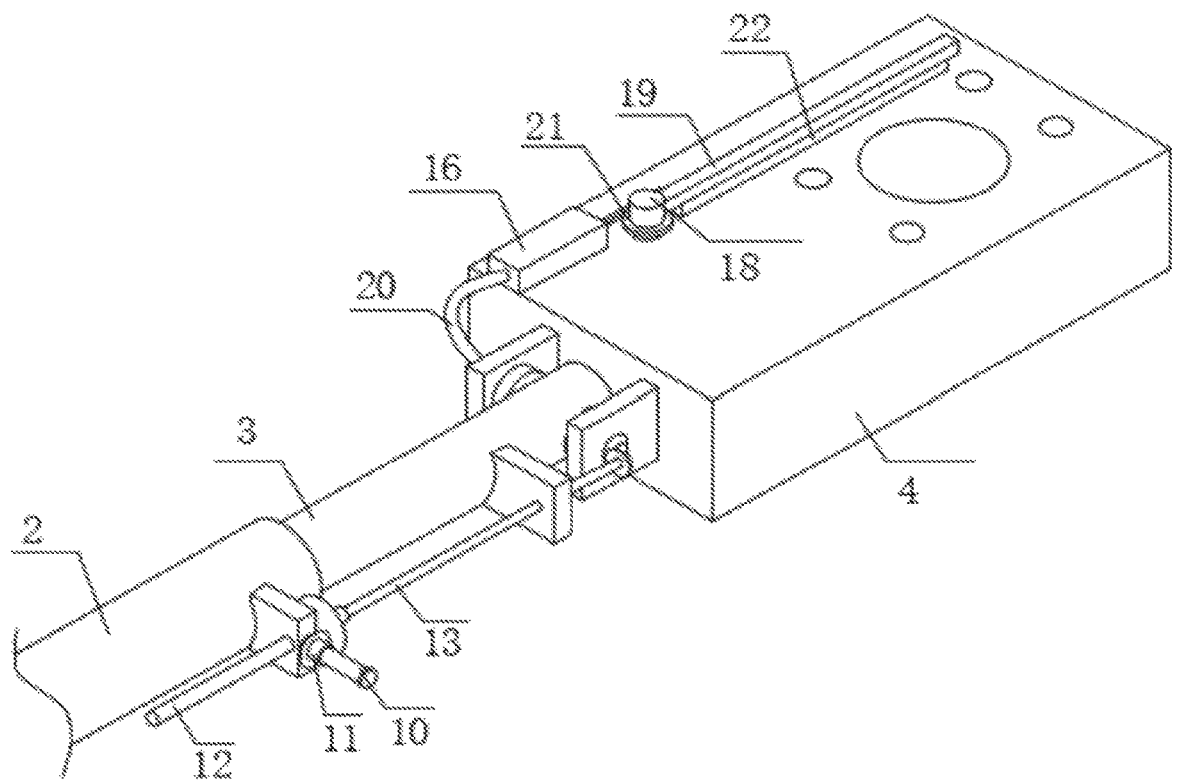
FIG. 2 is a three-dimensional diagram of a photo unit in FIG. 1.
Figure 3:
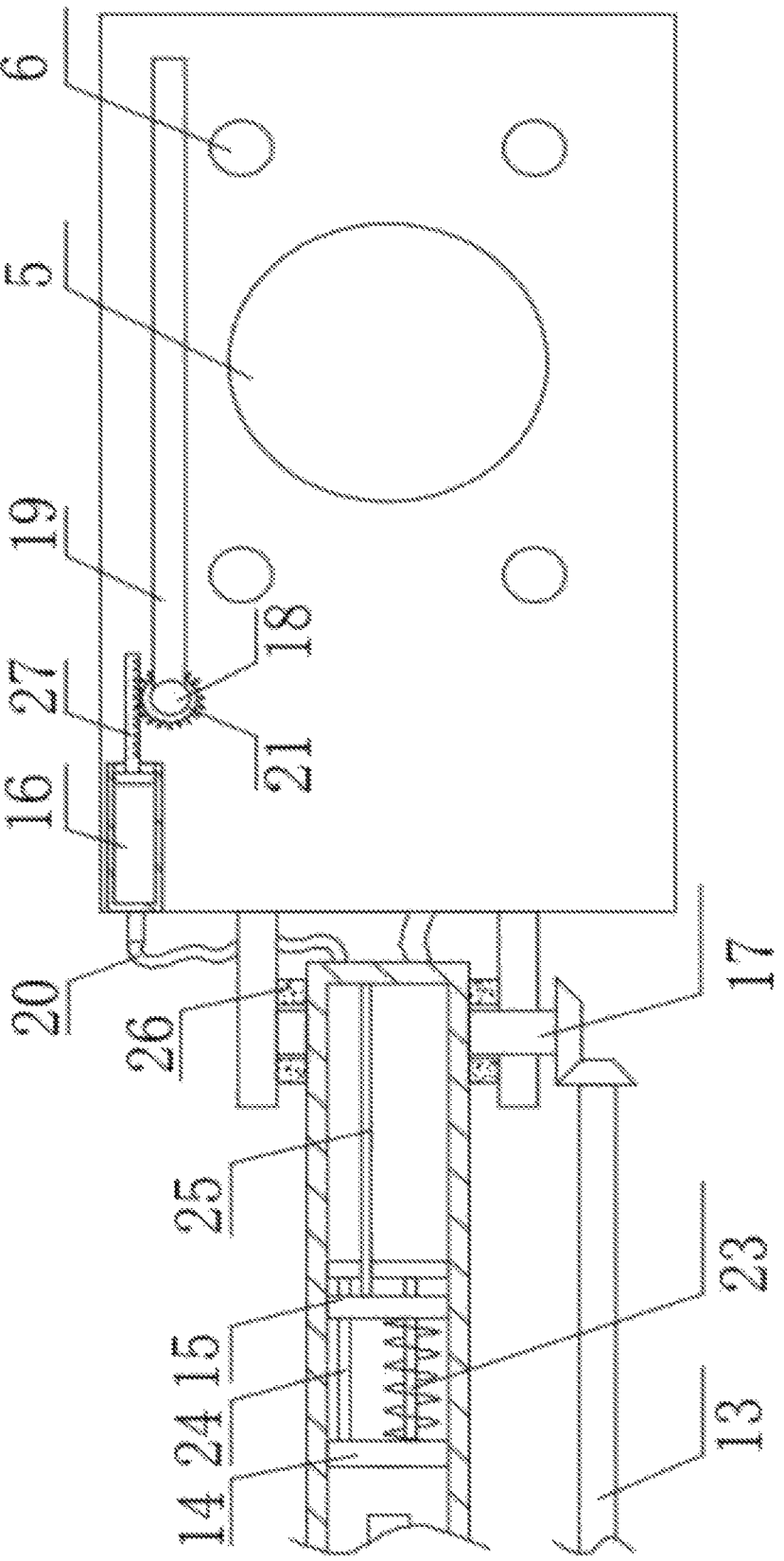
FIG. 3 is a structural sketch of an inflatable unit and a cleaning unit in FIG. 1.
Figure 4:
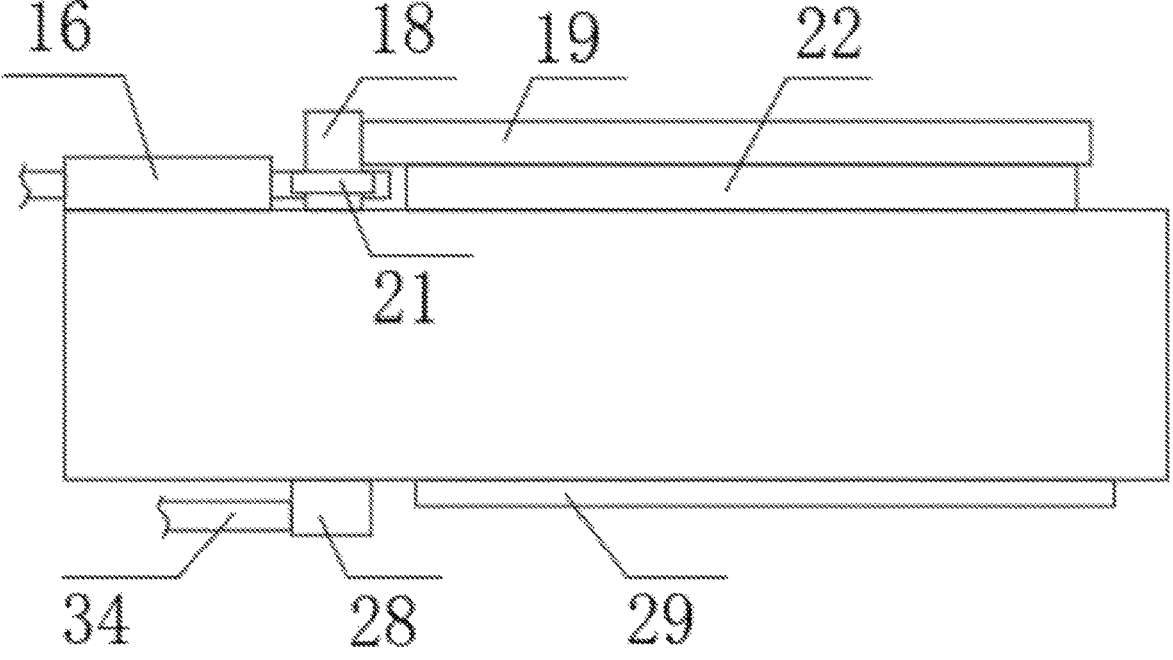
FIG. 4 is a side view of the photo unit.
Figure 5:
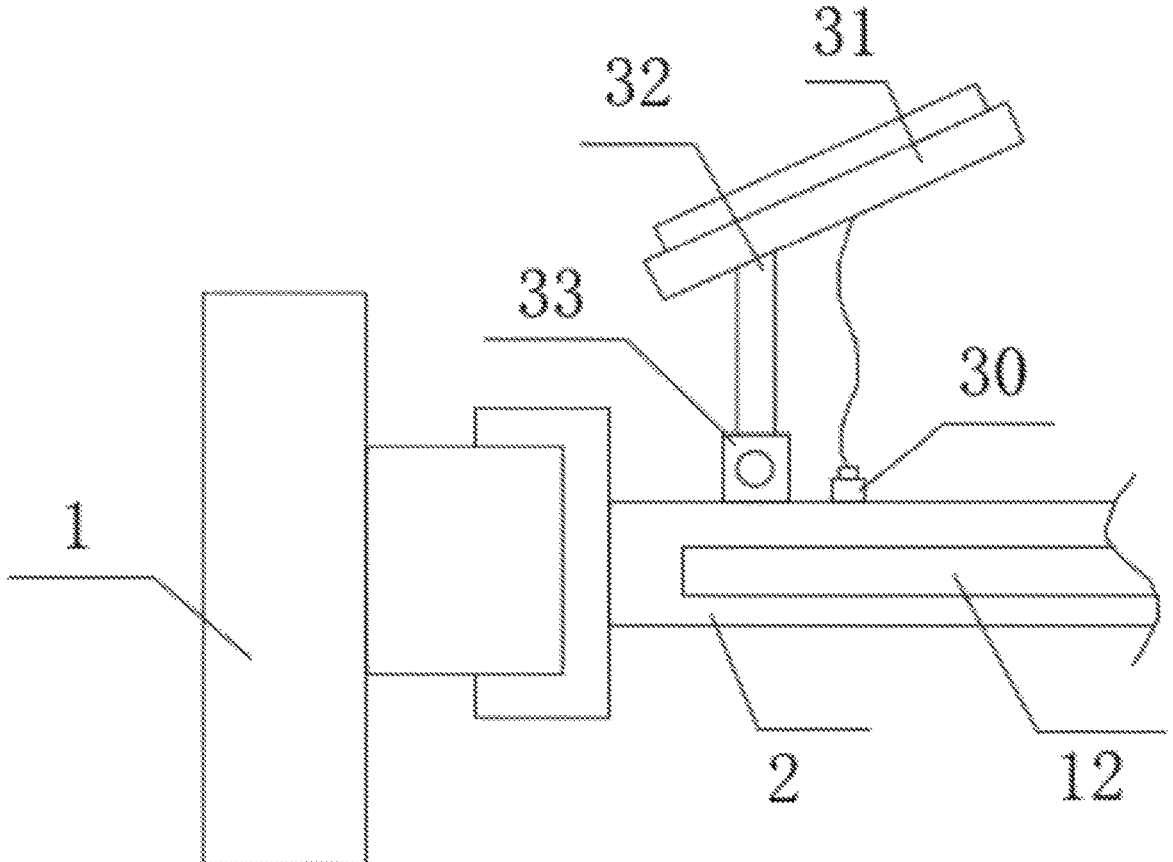
FIG. 5 is a structure diagram of a display unit.

Combined with FIGS. 1-3, the further improvement of this example on the basis of the example 1 is as follows: the base 4 is equipped with a cleaning unit, comprising a hollow shaft 18 interlinked with the base through rotational connection. A fixed pipe 19 is securely affixed to the periphery of the shaft 18, housing a cleaning brush 22 affixed to its underside. Outlet canals are situated on the bottom surface of the fixed pipe 19, oriented at a 45-degree angle relative to the top surface of the base 4. The cleaning brush 22 makes direct contact with the top surface of the base 4. Enhanced cleaning efficacy is achieved by initially removing dust from the top surface of the base 4 followed by wiping the same surface.

A purging unit is also incorporated within the movable column 3 to introduce air into the fixed pipe 19 and facilitate the rotation of shaft 18 when the movable column 3 contracts into the fixed cylinder 2. This purging unit comprises a fixed rod 8 positioned within the movable column 3, a sealing block 15 securely affixed to the inner side of the movable column 3, and a pneumatic component situated on the base 4 to drive a rotating shaft 18. Between the sealing block 15 and the inner wall of the movable column 3 near the base 4, a sealed gas storage space is established and fixed with a spacer plate 25, thus partitioning the gas storage space into gas chambers 1 and 2. The active block 14 is situated external to the gas storage space, with both the side adjacent to the sealing block 15 affixed with a piston rod 1 23 and a piston rod 2 24. One end of the piston rod 1 23 extends into gas chamber 1 and is affixed with a piston plate 1, while the other end of the piston rod 2 24 extends into gas chamber 2 and is affixed with a piston plate 2. An elastic component, in the form of a spring, is positioned around the outer sleeve of the piston rod 2 24 to facilitate the resetting of the active block 14. One end of the spring is fixed to the outer wall of the active block 14, while the other end is affixed to the outer wall of the sealing block 15. Moreover, one end of the fixed rod 8 is securely fixed to the inner wall of the fixed cylinder 2, and the fixed rod 8 collaborates with the active block 14. Additionally, the bottom of the base 4 is equipped with a connecting pipe 28, into which the bottom of the shaft 18 is inserted and connected. The periphery of the connecting pipe 28 is firmly linked with the gas pipe 2 34, with the other end of the gas pipeline 2 34 connected to the gas chamber 2 34, while the gas chamber 1 is connected to the pneumatic component.

The pneumatic component includes a piston cylinder 16 arranged on the top surface of the base 4, accommodating a piston plate 3 within. Additionally, a transmission rack 27 is affixed to the three outer walls of the piston plate 3, and a transmission gear 21 is encased around the shaft 18. One end of the transmission rack 27 extends beyond the piston cylinder 16 and meshes with the transmission gear 21. Furthermore, one end of the piston cylinder 16 is fitted with a gas pipeline 1 20, with its other end connected to the gas chamber 1.

The implementation principle of this example is as follows: Upon completion of the photography process, the movable column 3 retracts into the fixed cylinder 2. As the movable column 3 continues its retraction, the active block 14 makes contact with the fixed rod 8. Subsequently, under continued retraction, the active block 14 is compressed towards the side near the sealing block 15. This action drives the piston plate 1 and piston plate 2 to move within the gas chamber 1 and gas chamber 2, respectively. Consequently, gas within the gas chamber 1 is pressurized into the piston cylinder 16, initiating movement of the piston plate 3. Concurrently, the transmission rack 27 moves outward from the piston cylinder 16, driving rotation of the transmission gear 21. This rotation causes the fixed pipe 19 to rotate. Simultaneously, gas within the gas chamber 2 is pressurized into the shaft 18 and subsequently into the fixed pipe 19, where it is expelled through the outlet canal. This process dislodges dust from the top surface of the base 4, allowing the cleaning brush to effectively wipe the surface under the rotational motion of the fixed pipe 19.

When the movable column 3 is pulled out again, the spring undergoes deformation, thereby propelling the active block 14 to reset, moving it to the side distant from the sealing block 15. This action enables the gas within the piston cylinder 16 to be drawn back into the air chamber 1. Consequently, the transmission rack 27 moves inward into the piston cylinder 16, facilitating the retraction of the shaft 18 and the fixed pipe 19 to their original positions. Additionally, the gas chamber 2 is replenished with air.

The implementation method described above represents the preferred approach to implementing the invention and should not serve to limit the scope of protection afforded by the present invention. Any non-substantive changes and replacements made by technicians in this field on the basis of the present invention belong to the scope of protection required by the present invention.

What is claimed is:

1. An image acquisition system for health evaluation of lactating cow teats, comprising a guard plate, a telescopic column hinged onto the guard plate, and a photo unit mounted on the telescopic column; each of an end and an opposite end of the guard plate is equipped with a strap and features an installation seat at a rotational connection; the telescopic column comprises a fixed cylinder hinged onto the guard plate and a movable column housed within the fixed cylinder; one end of the movable column extends externally from the fixed cylinder, while a fixed grip is affixed to one side of an outer wall of the fixed cylinder, and a movable grip is attached to one side of an outer wall of the movable column;

the photo unit comprises a base hinged at one end of the movable column, a shooting device installed on the base and supplementary lights; the movable column is equipped with an adjustable unit for driving rotation of the base; the base is equipped with a cleaning unit;

the cleaning unit comprises a hollow shaft connected to the base by rotation, a fixed pipe affixed to a periphery of the hollow shaft, and a cleaning brush installed on a bottom surface of the fixed pipe; the bottom surface of the fixed pipe has outlet canals, and the fixed pipe is connected to the hollow shaft;

a purging unit is also installed in the movable column, serving to introduce air into the fixed cylinder and drive the hollow shaft to rotate when the movable column contracts into the fixed pipe;

a detachable display mounting frame is positioned on an outer surface of the fixed cylinder, housing a display screen linked to both the shooting device and supplementary lights.

2. The image acquisition system for health evaluation of lactating cow teats according to claim 1, wherein the base comprises a hollow structure housing the shooting device and supplementary lights, with mounting canals located on a top surface of the base; and lens of the shooting device and lampshades of the supplementary lights are aligned flush with the top surface of the base.

3. The image acquisition system for health evaluation of lactating cow teats according to claim 1, wherein the adjustable unit comprises a storage barrel that is rotatably connected to the fixed grip, a transmission rod that is rotatably linked to the outer wall of the movable column, and a movable sleeve positioned externally to the fixed grip; the movable sleeve is rotationally connected to the fixed grip, with an outer surface of the movable sleeve encasing a driving bevel gear, while an outer surface of the storage barrel is encased with a driven bevel gear that meshes with the driving bevel gear; one end of the transmission rod extends into the storage barrel and traverses along an axial direction of the storage barrel; two installation blocks are securely affixed to an outer wall of the base, with one end of the movable column situated between the two installation blocks; and each of both sides of the outer wall of the movable column is affixed with a connecting shaft that rotates along with each of the two installation blocks.

4. The image acquisition system for health evaluation of lactating cow teats according to claim 3, wherein the transmission rod positioned at one end of the storage barrel secures a limit block at a periphery of the transmission rod; a locating slot, set along an axial direction of the locating slot, is arranged on an inner wall of the storage barrel, where one end of the limit block extends into the locating slot and moves along with the locating slot; and an outer surface of the connecting shaft is encased with a friction ring, and one end of the friction ring is affixed to an outer wall of an installation block.

5. The image acquisition system for health evaluation of lactating cow teats according to claim 1, wherein the purging unit comprises a fixed rod positioned within the movable column, a sealing block affixed to an inner side of the movable column, and a pneumatic component mounted on the base to drive the hollow shaft to rotate; the purging unit establishes a sealed gas storage space between the sealing block and an inner wall of the movable column in proximity to the base; the sealed gas storage space is delimited by a spacer plate, thereby partitioning the sealed gas storage space into gas chamber 1 and gas chamber 2; positioned exterior to the sealed gas storage space, an active block is affixed with a piston rod 1 and a piston rod 2 on a side adjacent to the sealing block; a distal end of the piston rod 1 extends into the gas chamber 1 and is affixed with a piston plate 1, while a corresponding end of the piston rod 2 extends into the gas chamber 2 and is affixed with a piston plate 2; an outer sleeve of piston rod 2 features an elastic component designed to facilitate a reset of the active block; one end of the fixed rod is securely attached to an inner wall of the fixed cylinder, operating in conjunction with the active block; the base is equipped with a connecting pipe securely fixed at a bottom of the base, into which a bottom of the hollow shaft is inserted and connected; a periphery of the connecting pipe is firmly linked with a gas pipe 2, while an other end of the gas pipe 2 is connected with the gas chamber 2, and the gas chamber 1 is connected with the pneumatic component.

6. The image acquisition system for health evaluation of lactating cow teats according to claim 5, wherein the pneumatic component comprises a piston cylinder situated on a top surface of the base, a piston plate 3 actively positioned within the piston cylinder; the piston plate 3 is affixed with a transmission rack along three outer walls, while a transmission gear is encased outside the hollow shaft; one end of the transmission rack extends beyond the piston cylinder and engages with the transmission gear; and one end of the piston cylinder is outfitted with a gas pipe 1, an other end of the gas pipe 1 is connected to the gas chamber 1.

7. The image acquisition system for health evaluation of lactating cow teats according to claim 1, wherein a mounting sleeve is fixed on a top surface of the fixed cylinder, with an outer wall of the mounting sleeve secured by locking bolts; a bottom of the detachable display mounting frame is attached to an inserting rod, which is inserted into the mounting sleeve; one end of the locking bolts is connected to an outer wall of the inserting rod; and a data interface, connected to the supplementary lights and the shooting device, is installed on the outer wall of the fixed cylinder, allowing the display screen to be plugged into the data interface through a data line.

8. The image acquisition system for health evaluation of lactating cow teats according to claim 1, wherein a battery is incorporated within the base to supply power to both the shooting device and the supplementary lights; the battery is capable of being disassembled; a maintenance port is positioned at a bottom of the base, and the maintenance port is sealed by a detachable sealing cover on an exterior of the maintenance port.

9. The image acquisition system for health evaluation of lactating cow teats according to claim 1, wherein a chute is set along an axial direction on one side of the outer wall of the fixed cylinder, and an end of the movable grip extends through the chute to an outer side of the fixed cylinder.

* * * * *